(12) United States Patent
Zhang et al.

(10) Patent No.: US 10,420,346 B2
(45) Date of Patent: Sep. 24, 2019

(54) SILVER NANOPARTICLE-ENHANCED PHOTOSENSITIZERS

(71) Applicant: University Of Cincinnati, Cincinnati, OH (US)

(72) Inventors: Peng Zhang, Cincinnati, OH (US); Niranga Wijesiri, Cincinnati, OH (US); Hong Tang, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 0 days.

(21) Appl. No.: 16/011,154

(22) Filed: Jun. 18, 2018

(65) Prior Publication Data

US 2018/0295840 A1    Oct. 18, 2018

Related U.S. Application Data

(63) Continuation-in-part of application No. 15/123,549, filed as application No. PCT/US2015/016735 on Feb. 20, 2015, now Pat. No. 9,999,225.

(Continued)

(51) Int. Cl.
  *A61K 47/69*   (2017.01)
  *A01N 59/16*   (2006.01)
  (Continued)

(52) U.S. Cl.
  CPC .............. *A01N 59/16* (2013.01); *A01N 25/28* (2013.01); *A01N 43/34* (2013.01);
  (Continued)

(58) Field of Classification Search
  None
  See application file for complete search history.

(56) References Cited

U.S. PATENT DOCUMENTS 9,999,225 B2 *   6/2018   Zhang ................... A01N 59/16
2008/0215122 A1   9/2008   Geddes
(Continued)

FOREIGN PATENT DOCUMENTS

WO      03037297 A2    5/2003
WO    2008015453 A1    2/2008
(Continued)

OTHER PUBLICATIONS

Noorbakhsh et al.(Antifungal Effects of Silver Nanoparticles alone and with a combination of Antifungal Drug on Dermatophyte Pathogen *Trichophyton rubrum*, IPCBB vol. 5, 2011 (Year: 2011).*

(Continued)

*Primary Examiner* — Robert A Wax
*Assistant Examiner* — Melissa S Mercier
(74) *Attorney, Agent, or Firm* — Wood Herron & Evans LLP

(57) ABSTRACT

The present invention relates generally to compositions and methods of killing fungi using a surface plasmon coupled to a photosensitizer. A nanostructure (10) may include a silver nanoparticle core (12), a mesoporous silica shell (14), and a photosensitizer (16). A method of killing fungi may include contacting fungi with a nanostructure (10) including a silver nanoparticle core (12), a mesoporous silica shell (14), and a photosensitizer (16) to form a blend and exposing the blend to light.

5 Claims, 2 Drawing Sheets

Related U.S. Application Data

(60) Provisional application No. 61/949,509, filed on Mar. 7, 2014.

(51) Int. Cl.

| | |
|---|---|
| *A61K 41/00* | (2006.01) |
| *C07D 487/22* | (2006.01) |
| *C01G 5/00* | (2006.01) |
| *A01N 43/34* | (2006.01) |
| *A01N 25/28* | (2006.01) |
| *A01N 25/26* | (2006.01) |
| *B82Y 5/00* | (2011.01) |

(52) U.S. Cl.
CPC ...... *A61K 41/0057* (2013.01); *A61K 41/0071* (2013.01); *A61K 47/6923* (2017.08); *C01G 5/006* (2013.01); *C07D 487/22* (2013.01); *A01N 25/26* (2013.01); *B82Y 5/00* (2013.01); *C01P 2002/01* (2013.01); *C01P 2004/64* (2013.01)

(56) References Cited

U.S. PATENT DOCUMENTS

2009/0204057 A1   8/2009   Woo et al.
2009/0220423 A1   9/2009   Kurkayev

FOREIGN PATENT DOCUMENTS

WO         2010071831 A2    6/2010
WO     WO-2015134204 A1 *   9/2015   ............. A01N 59/16

OTHER PUBLICATIONS

Noorbakhsh et al. (Antifungal Effects of Silver Nanoparticles alone and with a combination of Antifungal Drug on Dermatophyte Pathogen *Trichophyton rubrum*, IPCBEE vol. 5. (2011)). (Year: 2011).*

Ragas, Xavier, et al., "Singlet Oxygen Phosphorescence Enhancement by Silver Islands Films," The Journal of Physical Chemistry, 2011, 115, pp. 16275-16281 (7 pages).

Schweitzer, Claude, et al., "Physical Mechanisms of Generation and Deactivation of Singlet Oxygen," Chem. Rev., 2003, vol. 103, pp. 1685-1757 (74 pages).

Shi et al., Photothermally enhanced photodymanic therapy based on mesoporous PD@Ag@mSi02, J. Mater.Chem B, 2013, 1, 1133; Published Dec. 18, 2012.

Smith, Kevin M. (University of Liverpool), "Porphyrins and Metalloporphyrins," Elsevier Scientific Publishing Company, 1975, Amsterdam-Oxford-New York (167 pages).

Soukos, Nikolaos S., et al., "Targeted Antimicrobial Photochemotherapy," Antimicrobial Agents and Chemotherapy, vol. 42, No. 10, Oct. 1998, pp. 2595-2601 (7 pages).

St. Denis, Tyler G., et al., "All you need is light—Antimicrobial photoinactivation as an evolving and emerging discovery strategy against infectious disease," Virulence, vol. 2:6, Nov./Dec. 2011, pp. 509-520 (13 pages).

Toftegaard, Rasmus, et al., "Metal nanoparticle-enhanced radiative transitions: Giving singlet oxygen emission a boost," Pure Appl. Chem., vol. 83, No. 4, pp. 885-898, 2011 (14 pages).

Toftegaard, Rasmus, et al., "Metal-Enhanced 1270 nm Singlet Oxygen Phosphorescence," Phosphorescent Enhancement, Angew. Chem. int. Ed. 2008, 47, pp. 6025-6027 (3 pages).

Turro, N.J., et al., "Modern Molecular Photochemistry of Organic Molecules," University Science Books, 2010, Table of Contents (2 pages).

Vankayala, Raviraj, et al., "Metal Nanoparticles Sensitize the Formation of Singlet Oxygen," Angew. Chem. Int. Ed., vol. 50, 2011, pp. 10640-10644 (5 pages).

Vankayala, Raviraj., et al., "Morphology dependent photosensitization and formation of singlet oxygen by gold and silver nanoparticles and its application in cancer treatment," Journal of Materials Chemistry B, 2013, 1, pp. 4379-4387 (9 pages).

Volman, David H., et al., "Advances in Photochemistry, vol. 14," John Wiley & Sons, Inc., 1988, Table of Contents (2 pages).

Wang, Tingting, et al., "Multifunctional Hollow Mesoporous Silica Nanocages for Cancer Cell Detection and the Combined Chemotherapy and Photodynamic Therapy," ACS Applied Materials & Interfaces, vol. 3, 2011, pp. 2479-2486 (8 pages).

Wiederrecht, Gary P., "Coherent Coupling of Molecular Excitons to Electronic Polarizations of Noble Metal Nanoparticles," Nano Letters, 2004, vol. 4, No. 11, pp. 2121-2125 (5 pages).

Xiao, Ling, et al., "Porous Silicon Nanoparticle Photosensitizers for Singlet Oxygen and Their Phototoxicity against Cancer Cells," ACS NANO, Mar. 31, 2011, pp. 3651-3659, vol. 5, No. 5, American Chemical Society (9 pages).

Xiu, Zong-ming, et al., "Negligible Particle-Specific Antibacterial Activity of Silver Nanoparticles," Nano Letters, vol. 12, 2012, pp. 4271-4275 (5 pages).

Yang, Yang, et al., "Lipid coated mesoporous silica nanoparticles as photosensitive drug carriers," Physical Chemistry Chemical Physics, vol. 12, 2010, pp. 4418-4422 (7 pages).

Zhang, Yongxia, et al., "Metal-Enhanced Phosphorescence: Interpretation in Terms of Triplet-Coupled Radiating Plasmons," J. Phys. Chem. B, vol. 110, 2006, pp. 25108-25114 (7 pages).

Zhang, Yongxia, et al., "Plasmonic engineering of singlet oxygen generation," PNAS, Feb. 12, 2008, vol. 105, No. 6, pp. 1798-1802 (5 pages).

Abdel-Shafi, Ayman A., et al., "Charge Transfer Effects on the Efficiency of Singlet Oxygen Production Following Oxygen Quenching of Excited Singlet and Triplet States of Aromatic Hydrocarbons in Acetonitrile," J. Phys. Chem. A, vol. 104, 2000, pp. 5747-5757 (11 pages).

Abdel-Shafi, Ayman A., et al., "Photosensitized Generation of Singlet Oxygen from Vinyl Linked Benzo-Crown-Ether-Bipyridyl Ruthenium(II) Complexes," J. Phys. Chem. A, Letters, vol. 104, 2000, pp. 192-202 (11 pages).

Adsorb definition (Wikitionary, accessed May 20, 2017).

Alves, Eliana, et al., "Charge effect on the photoinactivation of Gram-negative and Gram-positive bacteria by cationic meso-substituted porphyrins," BMC Microbiology, vol. 9:70, Apr. 2009 (13 pages).

Aslan, Kadir, et al., "Fluorescent Core-Shell Ag@SiO2 Nanocomposites for Metal-Enhanced Fluorescence and Single Nanoparticle Sensing Platforms," J. Am. Chem. Soc., vol. 129, 2007, pp. 1524-1525 (2 pages).

Brynildsen, Mark P., et al., "Potentiating antibacterial activity by predictably enhancing endogenous microbial ROS production," Nature Biotechnology Letters, vol. 31, No. 2, Feb. 2013, pp. 160-167 (8 pages).

Chen, Huanjun, et al., "Plasmon-molecule interactions," Nano Today, vol. 5, ScienceDirect, Aug. 2010, pp. 494-505 (12 pages).

Chen, Huanjun, et al., "Plasmonic-Molecular Resonance Coupling: Plasmonic Splitting versus Energy Transfer," The Journal of Physical Chemistry, vol. 116, 2012, pp. 14088-14095 (8 pages).

Chernousova, Svitlana, et al., "Silver as Antibacterial Agent: Ion, Nanoparticle, and Metal," Angewandte Chemie Int Ed. vol. 52, 2013, pp. 1636-1653 (18 pages).

Choi, Yeonho, et al., "Plasmon Resonance Energy Transfer (PRET)-based Molecular Imaging of Cytochrome c in Living Cells," Nano Letters, 2009, vol. 9, No. 1, pp. 85-90 (6 pages).

Chu, Zhiqin, et al., "Surface plasmon enhanced drug efficacy using core-shell Au@SiO2 nanoparticle carrier," Nanoscale, The Royal Society of Chemistry 2013, vol. 5, pp. 3406-3411 (6 pages).

Dahl, Thomas A., et al., "Comparison of Killing of Gram-Negative and Gram-Positive Bacteria by Pure Singlet Oxygen," Journal of Bacteriology, vol. 171, No. 4, Apr. 1989, pp. 2188-2194 (7 pages).

Darvill, Daniel, et al., "Plasmonic fluorescence enhancement by metal nanostructures: shaping the future of bionanotechnology," Phys. Chem. Chem. Phys., vol. 15, 2013, pp. 15709-15726, RSC Publishing (18 pages).

(56) References Cited

OTHER PUBLICATIONS

Demidova, Tatiana N., et al., "Effect of Cell-Photosensitizer Binding and Cell Density on Microbial Photoinactivation," Antimicrobial Agents and Chemotherapy, vol. 49, No. 6, Jun. 20058, pp. 2329-2335 (7 pages).
Derosa, Maria C. and Crutchley, Robert J., "Photosensitized singlet oxygen and its applications," Coordination Chemistry Review, Feb. 15, 2002, pp. 351-371, vol. 233-234, Elsevier (22 pages).
Derosa, Maria C., et al., "Photosensitized singlet oxygen and its applications," Coordination Chemistry Reviews 233-234 (2002) pp. 351-371 (21 pages).
Dolmans, Dennis E.J.G.L., et al., "Photodynamic therapy for cancer," Nat. Rev. Cancer, May 2003, vol. 3, pp. 380-387 (8 pages).
Eckhardt, Sonja, et al., "Nanobio Silver: Its Interactions with Peptides and Bacteria, and Its Uses in Medicine," Chemical Reviews, vol. 113, 2013, pp. 4708-4754 (47 pages).
Fofang, Nche T., et al., "Plexcitonic Nanoparticles: Plasmon-Exciton Coupling in Nanoshell-J-Aggregate Complexes," Nano Letters, 2008, vol. 8, No. 10, pp. 3481-3487 (7 pages).
Govorov, Alexander O., et al., "Hybrid Structures Composed of Photosynthetic System and Metal Nanoparticles: Plasmon Enhancement Effect," Nano Letters, 2007, vol. 7, No. 3, pp. 620-625 (6 pages).
Guo, Yanyan, et al., "Rose Bengal-decorated silica nanoparticles as photosensitizers for inactiviation of gram-positive bacteria," Nanotechnology, vol. 21, 2010, 065102 (7 pages).
Hamblin, Michael R., et al., "Photodynamic therapy: a new antimicrobial approach to infectious disease?," Photochem. Photobiol. Sci., May 2004, vol. 3(5), pp. 436-450 (30 pages).
Hamblin, Michael R., et al., "Polycationic photosensitizer conjugates: effects of chain length and Gram classification on the photodynamic inactivation of bacteria," Journal of Antimicrobial Chemotherapy, vol. 49, 2002, pp. 941-951 (12 pages).
Han, L., et al., "A facile one-pot synthesis of uniform core-shell silver nanoparticle @mesoporous silica nanospheres," Chem. Commun., vol. 47, 2011, pp. 8536-8538 (3 pages).
He, Qianjun, et al., "Mesoporous silica nanoparticle based nano drug delivery systems: synthesis, controlled drug release and delivery, pharmacokinetics and biocompatibility," Journal of Materials Chemistry, vol. 21, 2011, pp. 5845-5855 (11 pages).
Hocine et al., Silicates and mesoporous silica nanoparticles for photodynamic therapy, International Journal of Pharmaceutics, 402 (2010) 221-230.
Hu, Bo, et al., "Surface plasmon-photosensitizer resonance coupling: an enhances singlet oxygen production platform for broad-spectrum photodynamic inactivation of bacteria," Journal of Materials Chemistry B, 2014, vol. 2, pp. 7073-7081 (9 pages).
International Searching Authority, International Search Report and Written Opinion in PCT/US2015/016735 dated Apr. 8, 2015 (11 pages).
Jett, B.D., et al., "Simplified Agar Plate Method for Quantifying Viable Bacteria," Benchmarks, BioTechniques, vol. 23, Oct. 1997, pp. 648-655 (8 pages).
Jori, Giulio, et al., "Photosensitized inactivation of microorganisms," Photochem. Photobiol. Sci., vol. 3, 2004, pp. 403-405 (3 pages).
Kamat, Prashant V., "Photophysical, Photochemical and Photocatalytic Aspects of Metal Nanoparticles," J. Phys. Chem. B., 2002, 106, pp. 7729-7744 (16 pages).
Khaing OO, Maung Kyaw, et al., "Gold Nanoparticle-Enhanced and Size-Dependent Generation of Reactive Oxygen Species from Protoporphyrin IX," ASC Nano, vol. 6, No. 3, 2012, pp. 1939-1947 (9 pages).
Khlebtsov et al., Nanocomposites Containing Silica-Coated Gold-Silver Nanocages and Yb-2,4-dimethoxyhematoporphyrin: Multifunctional Capability of IR-Luminescence Detection, Photosensitization, and Photothermolysis; ASC NANO, vol. 5, No. 9, 7077-7089, 2011.
Kuimova, Marina K., et al., "Imaging intracellular viscosity of a single cell during photoinduced cell death," Nature Chemistry, vol. 1, Apr. 2009, pp. 69-73 (5 pages).
Lakowicz, Joseph R., "Radiative decay engineering 5: metal-enhanced fluorescence and plasmon emission," Anal Biochem, Feb. 15, 2005, vol. 337(2), pp. 171-194 (58 pages).
Lakowicz, Joseph R., "Radiative Decay Engineering: Biophysical and Biomedical Applications," Analytical Biochemistry 298, 2001, pp. 1-24 (24 pages).
Lambrechts, S.A.G., et al., "Mechanistic Study of the Photodynamic Inactivation of Candida albicans by a Cationic Porphyrin," Antimicrobial Agents and Chemotherapy, vol. 49, No. 5, May 2005, pp. 2026-2034 (9 pages).
Lin, Jing, et al., "Photosensitizer-Loaded Gold Vesicles with Strong Plasmonic Coupling Effect for Imaging-Guided Photothermal/Photodynamic Therapy," ACS Nano, vol. 7, No. 6, 2013, pp. 5320-5329 (10 pages).
Liu, Gang Logan, et al., "Quantized plasmon quenching dips nanospectroscopy via plasmon resonance energy transfer," Brief Communications, Nature Methods, vol. 4, No. 12, Dec. 2007, pp. 1015-1017 (1 page) Abstract Only.
Long, Ran, et al., "Surface Facet of Palladium Nanocrystals: A Key Parameter to the Activation of Molecular Oxygen for Organic Catalysis and Cancer Treatment," Journal of the American Chemical Society 2013, vol. 135 pp. 3200-3207 (8 pages).
Lyon, Juliana Pereira, et al., "Photodynamic therapy for pathogenic fungi," Mycoses, vol. 54, pp. e265-e271 (7 pages).
Maisch, T. et al., "Photodynamic Effects of Novel XF Porphyrin Derivatives on Prokaryotic and Eukaryotic Cells," Antimicrobial Agents and Chemotherapy, vol. 49, No. 4, Apr. 2005, pp. 1542-1552 (11 pages).
Maisch, Tim, "Anti-microbial photodynamic therapy: useful in the future?," Lasers Med Sci, vol. 22, 2007, pp. 83-91 (9 pages).
Ming, Tian, et al., "Plasmon-Controlled Fluorescence: Beyond the Intensity Enhancement," The Journal of Physical Chemistry Letters, 2012, 3, pp. 191-202 (12 pages).
Mori, Kohsuke, et al., "Enhancement of the Photoinduced Oxidation Activity of a Ruthenium(II) Complex Anchored on Silica-Coated Silver Nanoparticles by Localized Surface Plasmon Resonance," Angew. Chem. int. Ed., 2010, vol. 49, pp. 8598-8601 (4 pages).
Ni, Weihai, et al., "Coupling between Molecular and Plasmonic Resonances in Freestanding Dye-Gold Nanorod Hybrid Nanostructures," J. Am. Chem. Soc. 2008, vol. 130, pp. 6692-6693 (2 pages).
Ochsner, M., "Photophysical and photobiological processes in the photodynamic therapy of tumours," Journal of Photochemistry and Photobiology B: Biology 39, 1997 (18 pages).
Ogilby, Peter R., "Singlet oxygen: there is indeed something new under the sun," Chemical Society Reviews, 2010, vol. 39, pp. 3181-3209 (29 pages).
Pan, Shanlin, et al., "Enhancement of Platinum Octaethyl Porphyrin Phosphorescence near Nanotextured Silver Surfaces," J. Am. Chem. Soc., vol. 127, 2005, pp. 6087-6094 (8 pages).
Previte, Michael J.R., et al., "Metal-Enhanced Surface Plasmon-Coupled Phosphorescence," J. Phys. Chem. C, vol. 111, 2007, pp. 6051-6059 (9 pages).

* cited by examiner

SILVER NANOPARTICLE-ENHANCED PHOTOSENSITIZERS

RELATED APPLICATION

This application is a continuation-in-part of U.S. application Ser. No. 15/123,549, filed Sep. 2, 2016, which is in turn a National Stage entry application of application number PCT/US2015/016735 filed Feb. 20, 2015, which in turn claims priority to provisional application 61/949,509, filed Mar. 7, 2014, the disclosures of which are hereby incorporated by reference herein in their entirety.

STATEMENT REGARDING FEDERALLY SPONSORED RESEARCH OR DEVELOPMENT

This invention was made with government support under W81XWH-11-2-0103 awarded by United States Army Medical Research and Material Command. The government has certain rights in the invention.

TECHNICAL FIELD

The present invention relates generally to compositions and methods of killing bacteria and fungi and, more specifically, to compositions and methods of killing bacteria and fungi using a surface plasmon coupled to a photosensitizer.

BACKGROUND

Singlet oxygen plays a central role in many applications, such as photodynamic inactivation of microorganisms, photodynamic therapy of cancers, photoinduced oxidation, photodegradation of polymers, wastewater treatment, and fine chemical synthesis. Photodynamic inactivation (PDI) of bacteria has become an emerging and evolving strategy against infectious diseases, especially those related to multidrug resistance, because microorganisms do not appear to readily develop resistance toward PDI. In this regard, multidrug-resistant bacterial strains are shown to be killed by PDI as easily as their naïve counterparts. During PDI and when the level of the reactive oxygen species (ROS) produced exceeds bacterial detoxification and repair capabilities, the ROS can damage intracellular DNA, RNA, proteins, lipids, and cytoplasmic membrane, which leads to bacteria death.

Gram-positive and Gram-negative bacteria differ in membrane permeability due to the difference in the outer membrane structures. Gram-positive bacteria can easily take up most neutral or anionic photosensitizers and be readily photoinactivated, which is not the case for Gram-negative bacteria. This difference has led the development of photosensitizers toward polycationic conjugates or cationic photosensitizers to facilitate uptake by the bacterial cells. Importantly, some studies have shown that singlet oxygen, when produced sufficiently close to the bacteria, can diffuse into the bacteria cells causing fatal damage to the cells. Accordingly, photosensitizers with enhanced singlet oxygen production efficiency are highly desired, regardless of their charge properties.

The ground electronic state of molecular oxygen is a spin triplet. Ground-state (triplet) oxygen is not very reactive. However, triplet oxygen can be activated by the addition of energy and transformed into reactive oxygen species. The two electronically excited singlet states are $O_2$ ($^1\Delta_g$) and $O_2$ ($^1\Sigma_g^+$), at 94 and 157 kJ/mol above the ground state, respectively. The $O_2$ ($^1\Sigma_g^+$) state has a rather short lifetime, due to the spin-allowed transition to the $O_2$ ($^1\Delta_g$) state. The $O_2$ ($^1\Delta_g$) state is commonly referred to as singlet oxygen. Singlet oxygen has a relatively long lifetime (e.g. $10^{-6}$ to $10^{-3}$ seconds in solution) because of the spin-forbidden transition to the triplet state $O_2$ ($^3\Sigma_g^-$). Singlet oxygen can be observed experimentally in the absorption and emission at about 1270 nm.

The most convenient method of singlet oxygen production is the photosensitization of sensitizing molecules in the presence of light and oxygen. Great progress has been made in identifying, designing and synthesizing molecules as efficient photosensitizers. Even noble metal nanostructures have demonstrated the capability of singlet oxygen production. Still, the ability of noble metal nanostructures to enhance the production of singlet oxygen has remained largely unexploited. Since singlet oxygen plays a very important role in cell damage, an abundant supply of singlet oxygen is required.

Photodynamic inactivation of bacteria, among other applications that utilize singlet oxygen, is currently limited by the insufficient generation of singlet oxygen while reacting with biological targets. Accordingly, improved compositions and methods of producing singlet oxygen are needed to address the shortcomings of existing methods. More particularly, new compositions and methods are needed that increase the efficiency of the production of singlet oxygen.

Fungi are a large group of eukaryotic organisms distantly related to mammals, yet with similarities in the plasma membrane to that of mammalian cells. Most fungi have a rigid cell membrane including polysaccharides, such as chitin and ergosterol, whereas in mammalian cell membranes ergosterol is replaced by cholesterol. The similarities that exist between fungal and mammalian cell membranes render it challenging to develop antifungal drugs with low toxicity to humans.

*Tricophyton rubrum*, herein *T. rubrum*, is a dermatophytic fungus that commonly causes nail, skin and hair infections, i.e. dermatophytoses, due to its ability to utilize keratin. Fungal nail infection is the most common *T. rubrum* infection in humans worldwide, affecting 2%-13% of the world population. *T. rubrum* infections have indeed become a global phenomenon.

Fungal nail infection may be caused by a number of reasons, including less hygienic lifestyles, contact with infected skin scales, or contact with the fungi in wet areas such as swimming pools, showers and locker rooms. Infected patients may experience embarrassment in social and work situations, and carry the danger of transmitting the infection to others. Patients with diabetes, weakened immune system due to diseases such as HIV, and patients undergoing nail surgeries or cancer therapy, are highly susceptible to fungal nail infections, which could be serious, even fatal.

One drawback of existing drugs used to treat fungal infections is the relatively long-term treatments (some requiring up to 18 months to cure), and adverse side effects such as liver damage or drug interactions. Furthermore, the lack of targeted delivery of drugs may lead to less effective cure, as evidenced by slow and incomplete clearance of the infections. While molecular photosensitizers, such as methylene blue, toluidine blue, protoporphyrin and hematoporphyrin, have been shown to treat *T. rubrum* infections noninvasively, the use of molecular photosensitizers in PDI suffers from the drawback that most of the photosensitizers are highly hydrophobic and tend to aggregate in aqueous media, which reduces the efficiency of ROS generation and thus the efficacy of PDI.

Device-based treatments for fungal infections, such as laser treatments, iontophoresis, ultrasound treatments and photodynamic therapy, have been reported with varying degrees of success. So far, only laser treatments for cosmetic uses are FDA-approved. However, more studies are needed to validate the technique. The use of ultrasound devices has been investigated using a canine nail model. Still, the device itself seems complicated, and further studies will be required to assess it as a modality of antifungal treatment. Therefore, there is an ongoing need for noninvasive and user-friendly methods for treating of fungal infections.

SUMMARY

In its broadest aspects, embodiments of the present invention are directed to plasmon-photosensitizer resonance coupling hybrids. In one embodiment, a nanostructure includes a silver nanoparticle core, a mesoporous silica shell, and a photosensitizer. The photosensitizer may be covalently bonded to said silver nanoparticle. Further, the photosensitizer may be adsorbed onto said mesoporous silica shell.

Additionally, embodiments of the present invention are generally directed to photodynamic inactivation of microorganisms using singlet oxygen generated from the plasmon-photosensitizer hybrids. In an exemplary embodiment, a method of killing bacteria includes contacting bacteria with a nanostructure including a silver nanoparticle core, a mesoporous silica shell, and a photosensitizer to form a blend and exposing said blend to light. The bacteria may be Gram-positive or Gram-negative bacteria. The light may have a broad spectrum, the broad spectrum including visible and near infrared wavelengths.

A type of nanoparticle-based hybrid photosensitizers may be used to effectively inactivate fungi. For example, dermatophyte *T. rubrum* is one of the common fungi that can cause infections of the skin, including fungal nail infection. *T. rubrum* infection can transmit by direct contact with the infected skin. Therefore, it has become one of the most common infections worldwide. PDI is one of the promising approaches for the treatment of this type of infections. Described herein is a novel method of PDI against *T. rubrum* by using nano-particle-based hybrid photosensitizers.

In another exemplary embodiment, a method of killing fungi includes contacting fungi with a nanostructure including a silver nanoparticle core, a mesoporous silica shell, and a photosensitizer to form a blend and exposing said blend to light. The light may have a broad spectrum, the broad spectrum including visible and near infrared wavelengths.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Embodiments of the present invention are directed to a surface plasmon-photosensitizer hybrid. Further embodiments of the present invention are directed to a method of killing bacteria that includes a surface plasmon-photosensitizer hybrid. Further embodiments of the present invention are directed to a method of killing fungi that includes the surface plasmon-photosensitizer hybrid. The surface plasmon-photosensitizer hybrid includes metal nanoparticles, an inert porous layer, and a photosensitizer.

The core of the surface plasmon-photosensitizer hybrid consists of metal nanoparticles. The metal nanoparticles may be, for example, silver nanoparticles (AgNPs). The diameter of the AgNP core may be, for example, about 10 to 50 nm.

The metal nanoparticles may be coated with the inert porous layer, or shell, to create a nanostructure. The porous layer may be further considered to be mesoporous, meaning the layer includes pores having a diameter generally in the range of about 2 to 50 nm. The thickness of the resulting mesoporous $SiO_2$ shell may be, for example, about 10 to 100 nm.

The nanostructure may be subsequently coated with a photosensitizer. Embodiments of the present invention may include a variety of photosensitizers. By way of example and without limitation, the photosensitizer could include tris(2, 2'-bipyridyl)dichlororuthenium(II) hexahydrate (RuBPy), rose bengal (RB), hematoporphyrin IX dihydrochloride (HPIX), meso-tetra(4-carboxyphenyl) porphine (TCPP), Cu(II) meso-tetra(4-carboxyphenyl) porphine (Cu-TCPP), meso-porphyrin IX (PIX), protoporphyrin IX (PPIX), erythrosin B, hem in, and riboflavin. Some of these structures are shown below.

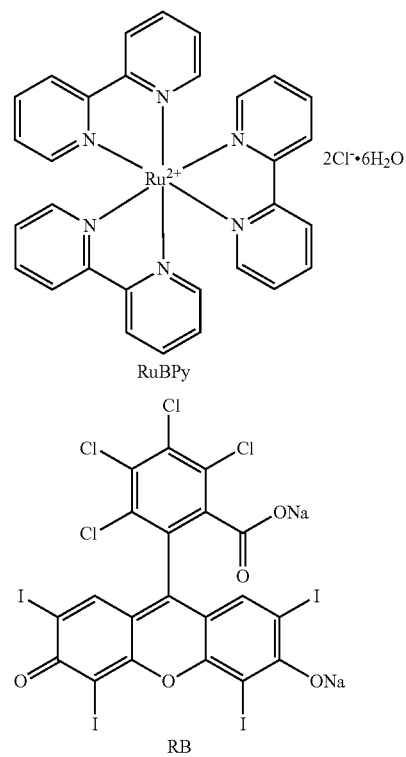

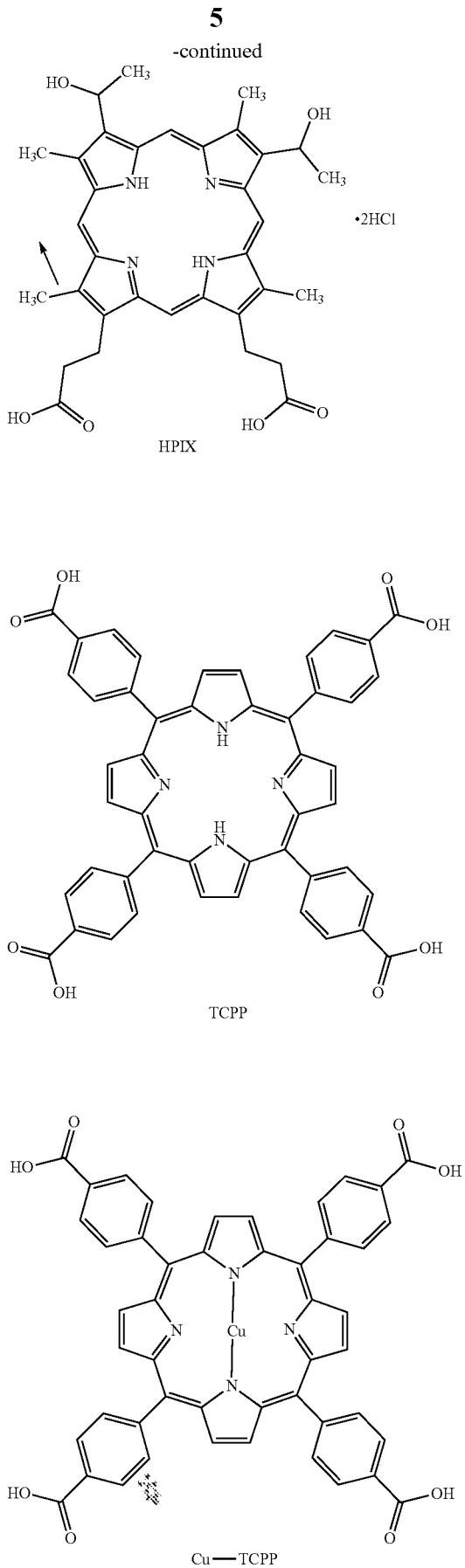

HPIX

TCPP

Cu—TCPP

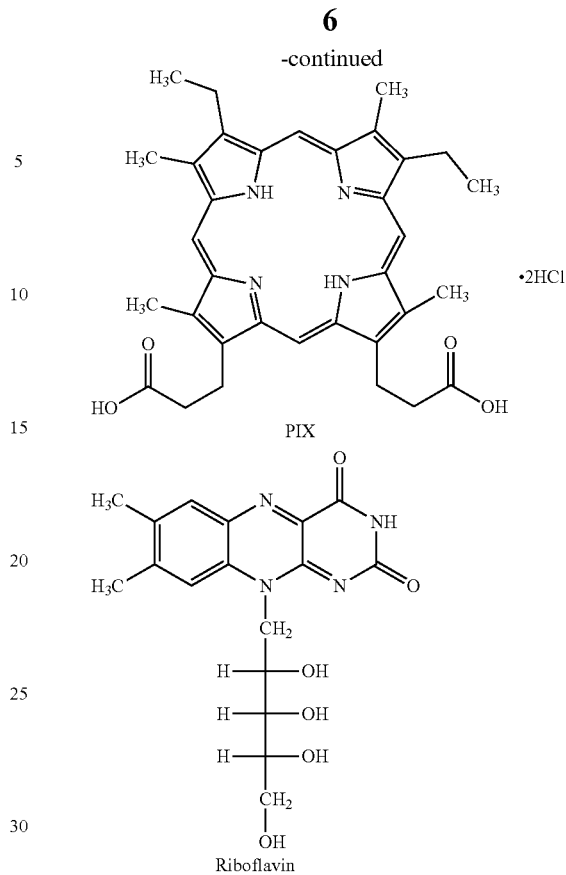

PIX

Riboflavin

Figure 1:
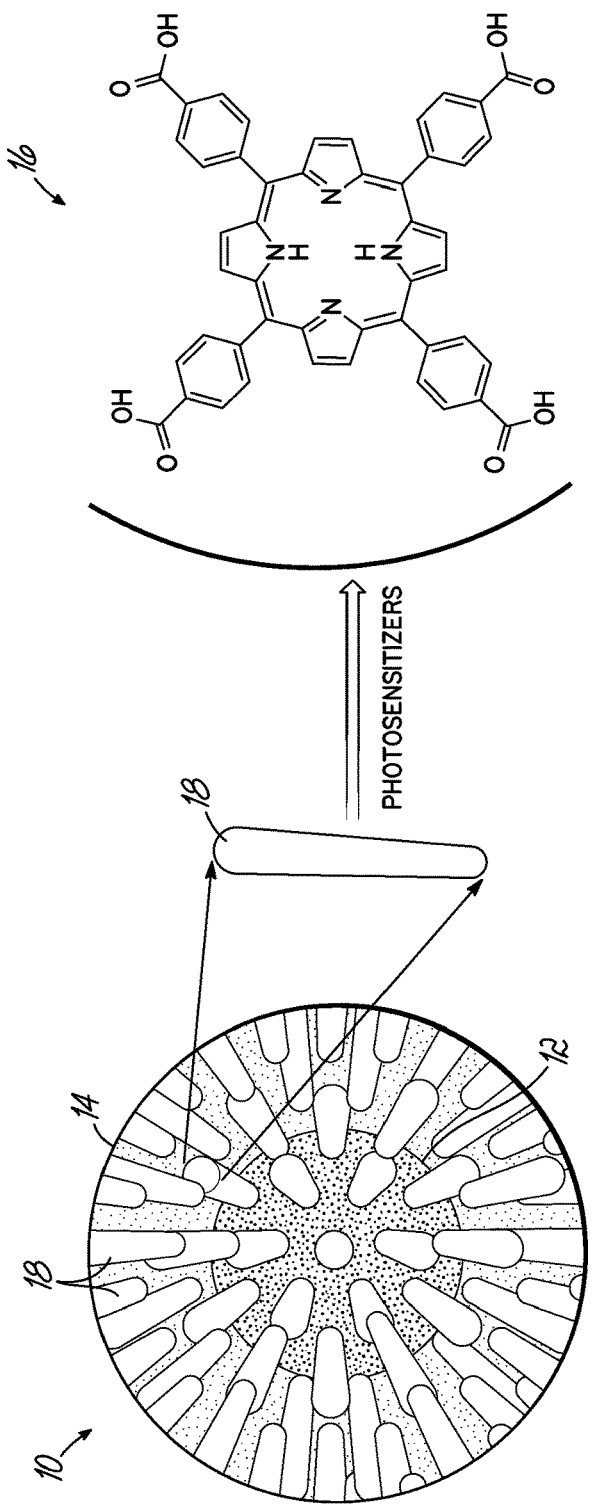
FIG. 1 is a schematic representation of a nanostructure according to an embodiment of the present invention.

FIG. 1 shows a schematic representation of a surface plasmon-photosensitizer hybrid 10 having a metal nanoparticle core 12, a mesoporous shell 14, and a photosensitizer 16 that may be adsorbed in the mesopores 18 of the shell 14. The adsorption of the photosensitizer takes advantage of the enormous porosity and surface area of the mesoporous nanostructures. The mesopores in the inert shell are capable of hosting the photosensitizers and facilitate the interaction between the photosensitizers and the metal nanoparticles. The loading efficiency of the photosensitizer may vary based on differences in photosensitizer properties. Further, different photosensitizers may display different degrees of resonance coupling with AgNPs, depending on the overlap of the surface plasmon and the absorption spectra of the photosensitizers.

In an exemplary embodiment of the present invention, silver nanoparticles (AgNPs) may be prepared inside a mesoporous silica matrix to create silver-mesoporous silica core-shell nanoparticles (Ag@mSiO$_2$). More specifically, Ag@mSiO$_2$ nanoparticles may be synthesized by a facile method using, for example, silver nitrate as the precursor, formaldehyde as the reducing agent, cetyltrimethylammonium bromide (CTAB) as the stabilizer and template, tetraethyl orthosilicate (TEOS) as the silica source, and sodium hydroxide (NaOH) as the catalyst. Those of ordinary skill in the art will appreciate that the silver-mesoporous silica core-shell nanoparticles may be fabricated using other methods.

Figure 2:
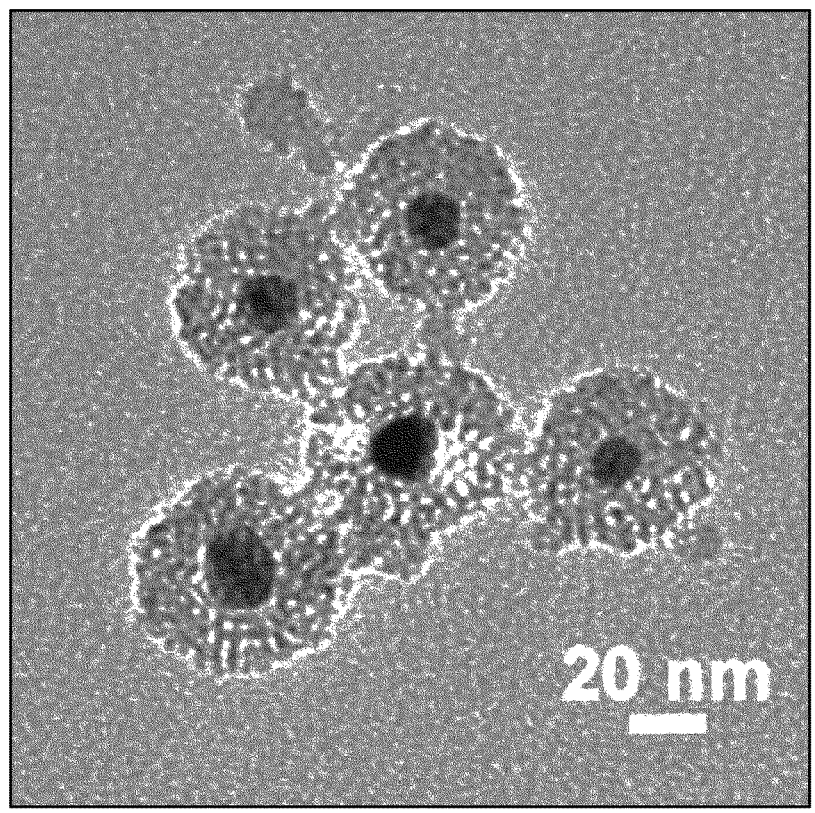
FIG. 2 illustrates a nanostructure according to an embodiment of the present invention.

After synthesis, Ag@mSiO$_2$ nanoparticles may be dispersed in an aqueous solution under stirring. Next, a solution of a photosensitizer may be added and stirred for a suitable period of time. The products may then be centrifuged and washed to remove any unbound photosensitizers. Finally, the as-synthesized Ag@mSiO$_2$@photosensitizer hybrids may be dispersed into an aqueous solution under sonication. FIG. 2 is a TEM image of an exemplary spherical Ag@mSiO$_2$@photosensitizer hybrid with an average particle size of 47 nm.

In a typical singlet oxygen production process, a photosensitizer is excited to the excited singlet state and subsequently reaches the excited triplet state via intersystem crossing (ISC). When encountering ground state (triplet) molecular oxygen, energy transfer takes place between the excited triplet state of the photosensitizer and molecular oxygen, leading to the generation of singlet oxygen. Experimentally, the observed singlet oxygen phosphorescence intensity can be described by Equation (1):

$$I = \gamma_{ex} \cdot \Phi_{ISC} \cdot P_T^{O_2} \cdot S_A \cdot \Phi_p \cdot \varepsilon_{coll}$$

where $\gamma_{ex}$ is the excitation rate, (Disc is the ISC efficiency of the photosensitizer, $P_T^{O_2}$ is the fraction of the triplet photosensitizers reacted with ground state oxygen, $S_A$ is the efficiency of the interaction between triplet photosensitizers and ground state oxygen that results in the formation of singlet oxygen, $\Phi_p$ is the phosphorescence emission quantum yield of the singlet oxygen, and $\varepsilon_{coll}$ is the light collection efficiency of the instrument. Further, $P_T^{O_2}$ can be described by Equation (2):

$$P_T^{O_2} = \frac{k_q \cdot [O_2]}{\tau^{-1} + k_q \cdot [O_2]}$$

where $k_q$ is the rate constant of the triplet photosensitizer reacting with the ground state oxygen, $[O_2]$ is the ground state oxygen concentration, and $\tau$ is the lifetime of triplet photosensitizer in the absence of oxygen.

Hybrids according to the present invention may generally demonstrate significant enhancement in singlet oxygen production, and thus in the observed singlet oxygen phosphorescence intensity, as compared to pure photosensitizers. This is due in part to the advantageous plasmon-molecular resonance coupling where the light-absorbing molecules near the metal nanoparticles exhibit strong absorption due to the localized surface plasmon. In other words, increased spectral overlap between the surface plasmon resonance spectrum of the silver core and the absorption spectra of the photosensitizer results in increased singlet oxygen production. Strong resonance coupling between the photosensitizers and silver core may increase the singlet oxygen production by up to three orders of magnitude.

The presence of AgNP in the vicinity of the photosensitizers has differing effects on the components of the observed singlet oxygen phosphorescence intensity (I). For example, the phosphorescence of the surface plasmon of the AgNP core, at about 403 nm, is far from the singlet oxygen phosphorescence of 1270 nm, which suggests little resonance between the surface plasmon and the singlet oxygen. Thus, it is expected that $\Phi_p$ remains unchanged regardless of the presence of the AgNP core. Further, the light collection efficiency term, $\varepsilon_{coll}$, is system-dependent and should be generally constant if the measurements are conducted under the same experimental settings. As will be described below, the presence of AgNP in the vicinity of the photosensitizers may enhance the other three variables in the photosensitization process—$\gamma_{ex}$, $P_T^{O_2}$, and $S_A$.

The enhancement in the excitation rate of photosensitizers, $\gamma_{ex}$, is possible in Ag@mSiO$_2$@photosensitizer hybrids where the photosensitizers are adsorbed into the mesopores with close proximity to the AgNP core. The excitation of the surface plasmon resonance can greatly enhance the local electromagnetic field near the surface of the AgNPs. With a good spectral overlap between the surface plasmon of AgNP and the absorption of the photosensitizer, the photosensitizers will experience an enhanced excitation, resulting in the increase of $\gamma_{ex}$.

The fraction of the triplet photosensitizers reacted with ground state oxygen ($P_T^{O_2}$) may increase because the reaction of the excited hybrid with molecular oxygen occurs in the mesopores of the silica. The small volume of the pores results in increased collision frequency. The pores may have, for example, a mean diameter of 2.5 nm and a mean length of 17 nm.

Interaction between the excited triplet photosensitizer and ground state oxygen is essentially a triplet-triplet annihilation process with $S_A$ being the efficiency. It has long been understood that triplet-triplet encounter complexes produce nine spin states of singlet, triplet, and quintet, with a statistical probability of ⅑, ⅜ and ⅝, respectively. The singlet channel is the only path leading to singlet oxygen. However, intersystem crossing among different spin states of the encounter complex is possible, which has been proposed to explain the quenching rate constant higher than ⅑ of the diffusion rate constant in the literature. In that regard, the presence of AgNPs could promote, through heavy atom effect, the intersystem crossing in the triplet-triplet encounter complex, leading to a higher probability toward the singlet channel and a higher S.

Hybrids according to the present invention may have other advantageous properties associated with singlet oxygen production. Singlet oxygen production may increase linearly with the increased concentration of hybrids, indicating little self-quenching at higher concentrations. In contrast, singlet oxygen production does not linearly increase with the increased concentrations of pure photosensitizers, which indicates strong self-quenching at higher concentrations. Furthermore, hybrids may display good stability in singlet oxygen production over a long illumination time, with no decay in activity. Because of these advantageous properties, hybrids according to the present invention may be useful in more applications than pure photosensitizers.

The surface plasmon-photosensitizer hybrids may have new spectral characteristics as compared to pure photosensitizers. The hybrid state(s) formed by the surface plasmon-molecular resonance coupling may markedly affect the fluorescence of the photosensitizers. For example, there may be significant changes in the fluorescence emission and excitation spectra of the hybrids, both in intensity and shape. The high-energy Soret band (B-band) and the low-energy quasi-allowed band (Q-band) transitions in the excitation spectra may both decrease significantly. The emission bands may be broadened and weakened. Generally, as the concentrations of photosensitizer increase, the fluorescence intensities decrease due to severe self-quenching. In contrast, Ag@mSiO$_2$@photosensitizer hybrids may display only slight change both in fluorescence intensity and shape when the concentration increases as compared to the pure photosensitizer.

Another embodiment of the present invention includes a method of killing bacteria. Bacteria may be contacted with a surface plasmon-photosensitizer hybrid according to the present invention. Next, the bacteria and hybrid may be exposed to light causing the Ag@mSiO$_2$@photosensitizer hybrid to produce singlet oxygen, which results in photodynamic inactivation of the bacteria. Advantageously, the Ag@mSiO$_2$@photosensitizer hybrids may generally demonstrate significant enhancement in singlet oxygen production and an increased efficiency in the photodynamic inactivation of the bacteria. The highly improved PDI efficiency of the Ag@mSiO$_2$@photosensitizer hybrids may be understood in the following aspects. First, the adsorbed photosensitizers in the mesopores of silica matrix may result in a high local concentration (e.g. 1,600 photosensitizers per particle in Ag@mSiO$_2$@HPIX hybrids). Second, the surface plasmon-photosensitizer coupling may enhance the singlet oxygen production efficiency. Third, the locally generated singlet oxygen may reach a higher concentration than when free photosensitizers act individually, causing more damage to the bacteria. There are other advantages of using hybrids according to the present invention for PDI, in addition to the improved efficiency against broad-spectrum bacteria. For example, a non-coherent white light source may be used. Further, there is no incubation time required for the uptake of the hybrid by the bacteria. Moreover, using a hybrid may allow photosensitizers that are insoluble in water to be utilized in PDI applications.

In an exemplary embodiment, a culture of bacteria may be inoculated and mixed with a Ag@mSiO$_2$@photosensitizer hybrid. The bacteria may be, for example, Gram-positive or Gram-negative. The culture may then be illuminated with an appropriate fluence. Advantageously, the applied light may have a broad spectrum including, for example, visible and near infrared wavelengths. Some pure photosensitizers, such as Riboflavin, need visible light excitation to display a rather moderate antibacterial effect. Consequently, the spectral window of excitation may be broadened when using hybrids according to the present invention. As a result, a variety of light sources may be used in practice instead of light sources with specific wavelengths.

Another embodiment of the present invention includes a method of inactivating fungi. Fungi may be contacted with a surface plasmon-photosensitizer hybrid according to the present invention. Next, the fungi and hybrid may be exposed to light causing the Ag@mSiO$_2$@photosensitizer hybrid to produce singlet oxygen, which results in photodynamic inactivation of the fungi. Advantageously, the Ag@mSiO$_2$@photosensitizer hybrids may generally demonstrate significant enhancement in singlet oxygen production and an increased efficiency in the photodynamic inactivation of the fungi. The highly improved PDI efficiency of the Ag@mSiO$_2$@photosensitizer hybrids may be understood in the following aspects. First, the adsorbed photosensitizers in the mesopores of silica matrix may result in a high local concentration (e.g. 1,600 photosensitizers per particle in Ag@mSiO$_2$@HPIX hybrids). Second, the surface plasmon-photosensitizer coupling may enhance the singlet oxygen production efficiency. Third, the locally generated singlet oxygen may reach a higher concentration than when free photosensitizers act individually, causing more damage to the fungi. There are other advantages of using hybrids according to the present invention for PDI, in addition to the improved efficiency against at least some fungi. For example, a non-coherent white light source may be used. Further, there is no incubation time required for the uptake of the hybrid by the fungi. Moreover, using a hybrid may allow photosensitizers that are insoluble in water to be utilized in PDI applications.

In an exemplary embodiment, a culture of fungi may be inoculated and mixed with a Ag@mSiO$_2$@photosensitizer hybrid. The culture may then be illuminated with an appropriate fluence. Advantageously, the applied light may have a broad spectrum including, for example, visible and near infrared wavelengths. Some pure photosensitizers, such as Riboflavin, need visible light excitation to display a rather moderate antibacterial effect. Consequently, the spectral window of excitation may be broadened when using hybrids according to the present invention. As a result, a variety of light sources may be used in practice instead of light sources with specific wavelengths.

In some examples, the hybrid photosensitizers may include a silver-core mesoporous silica-coated nanoparticles with hydrophobic photosensitizing molecules, Hematoporphyrin IX dihydrochloride, adsorbed in the pores (noted as Ag@mSiO$_2$@HPIX) adsorbed in the pores. The hydrophilic surface of the silica nanoparticles allows them to be well dispersed in aqueous media, while the silver nanoparticle (AgNP) core displays plasmonic enhancement to the ROS generation of the photosensitizing molecules. Due to the strong resonance coupling between the silver core and HPIX, Ag@mSiO$_2$@HPIX hybrids display enhanced singlet oxygen generation and high PDI efficacy against fungi. Herein, we show that the combination of the Ag@mSiO$_2$@HPIX hybrids and a hand-held LED (power intensity of ~50 mW/cm2) can effectively inactivate fungi, such as *T. rubrum* (ATCC 28188).

In order to facilitate a more complete understanding of the embodiments of the invention, the following non-limiting examples are provided.

Example 1

Synthesis of Ag@mSiO$_2$ Nanoparticles.

Silver-mesoporous silica core-shell nanoparticles (Ag@mSiO$_2$) were synthesized by a facile method using silver nitrate as the precursor, formaldehyde as the reducing agent, CTAB as the stabilizer and template, TEOS as the silica source, and sodium hydroxide as the catalyst. In a typical run, 0.02 g of CTAB was dissolved in a solution containing 9.8 mL of water and 0.24 mL of 0.5 M NaOH. After stirring at 80° C. for 10 min, 0.06 mL of 1.0 M formaldehyde solution and 0.24 mL of 0.1 M silver nitrate aqueous solution were added. Then, 0.07 mL TEOS was added at a rate of 3 mL/h under stirring. After the reaction progressed at 80° C. under stirring for 2 h, the products were centrifuged and washed by ethanol. The surfactant template was removed by extraction in ethanol solution containing ammonium nitrate (6 g/L) at 50° C. for 30 min.

Synthesis of Ag@mSiO$_2$@photosensitizer Hybrids.

The freshly synthesized Ag@mSiO$_2$ nanoparticles were dispersed in 10 mL aqueous solution under stirring. Then, 10 mL of a DMF solution of respective photosensitizer (1 mM) was added, and the solution was stirred at room temperature for 72 h. The photosensitizers used include tris(2,2'-bipyridyl)dichlororuthenium(II) hexahydrate (RuBPy), rose bengal (RB), hematoporphyrin IX dihydrochloride (HPIX), meso-tetra(4-carboxyphenyl) porphine (TCPP), Cu(II) meso-tetra(4-carboxyphenyl) porphine (Cu-TCPP), and meso-porphyrin IX (PIX). FIG. 2 illustrates the structures of these six photosensitizers. The products were centrifuged and washed by water and DMF three times to remove any unbound photosensitizers. Finally, the synthesized Ag@mSiO$_2$@photosensitizer hybrids were dispersed into 10 mL aqueous solution under sonication to be used as stock solutions.

Loading Efficiency and Zeta Potential Measurements.

The loading efficiencies of the photosensitizers in the hybrids were determined by UV-Vis absorption. As previously discussed, the loading efficiencies of the six photosensitizers into the mesoporous silica pores differ due to the diverse molecular structures. TCPP, Cu-TCPP and PIX had higher loading efficiencies of 140.7 μg/mg, 260.5 μg/mg, and 750 μg/mg, respectively; while HPIX, RuBPy and RB had lower loading efficiencies of 27.4 μg/mg, 28.3 μg/mg, and 33.6 μg/mg, respectively. Zeta potential measurements were carried out to further investigate the surface properties of the hybrids. The zeta potential of the initial Ag@mSiO$_2$ core-shell nanoparticles was −26.44 mV. The zeta potentials of the hybrids containing HPIX, TCPP, Cu-TCPP, PIX, RuBPy, and RB are −25.65 mV, −35.46 mV, −36.45 mV, −35.39 mV, −5.8 mV, and −31.78 mV, respectively. The results show that the presence of the adsorbed photosensitizers had only moderate effect on the zeta potential of the Ag@mSiO$_2$ nanoparticles, except for RuBPy.

Silver Ion Release Measurements.

A dispersion of Ag@mSiO$_2$ nanoparticles (about 1.1 mg/mL) was prepared in diluted HNO$_3$ solution (pH 4.0), which can accelerate the oxidation of AgNPs under the ambient conditions and the release of Ag$^+$ into solution. The solution was exposed to air for 5 days, and one sample was collected each day. The released Ag$^+$ concentration of each sample was measured by inductively coupled plasma-mass spectrometry (ICP-MS).

Fluorescence and Phosphorescence Measurements.

A QM-40 spectrofluorometer (PTI Inc.) equipped with a high performance InGaAs photodiode and a lock-in amplifier (MODEL 410 single phase, Scitec Instruments Ltd.) was used to measure the fluorescence and phosphorescence spectra and lifetimes. Detection of the singlet oxygen production was carried out by monitoring its phosphorescence emission at about 1270 nm. The light source was a Xenon arc lamp, the output of which passed through an optical chopper operating at a fixed frequency. Samples were loaded into a quartz cuvette and placed in a light-tight chamber, with the emission signal collected orthogonal to the excitation beam. An additional long-pass filter (850 nm cut-off) was used to remove any possible higher-order artifact signals. Samples were dispersed in DI water for testing. To remove the silver core from the Ag@mSiO$_2$@photosensitizer hybrids, an excess amount of sodium cyanide (0.1 M) was added, which itself would not affect the photosensitizers adsorbed into the mesoporous silica. All fluorescence, phosphorescence, and lifetime measurements of Ag@mSiO$_2$@photosensitizer hybrids were carried out on the same instrument. All photosensitizers were dissolved in PBS buffer solution (pH 7.4) before spectral measurement. The excitation wavelengths for fluorescence and singlet oxygen production are 403 nm, 400 nm, 400 nm, 393 nm, 460 nm, and 550 nm for HPIX, TCPP, Cu-TCPP, PIX, RuBPy, and RB, respectively. The emission bands center at 620 nm, 650 nm, 650 nm, 617 nm, 615 nm, and 576 nm, for HPIX, TCPP, Cu-TCPP, PIX, RuBPy, and RB, respectively.

Photodynamic Inactivation Assays.

Typically, overnight cultures of *Staphylococcus epidermidis* (ATCC 35984), *Escherichia coli* (ATCC 35218), and *Acinetobacter baumannii* (ATCC 19606) were inoculated into PBS buffer solution (pH=7.4) and mixed with a series of concentrations of Ag@mSiO$_2$@HPIX hybrid, HPIX (dissolved in the same PBS buffer solution), or Ag@mSiO$_2$ nanoparticles. All bacterial suspensions (200 μL) were then placed in the wells of 96-well plates. The final cell concentration of the suspensions was between about 10$^6$ and 10$^7$ colony-forming units per mL (CFU/mL). The wells were illuminated with different fluences. After illumination, a plate count was performed. Bacterial viability was determined by a modified version of the Miles and Misra method.

The suspensions were serially 10-fold diluted with PBS. Then, drops of 10 μL of each dilution were applied onto MH II agar plates. Plates were streaked in triplicate and incubated for 18-24 h at 37° C. in the dark before counting. A non-coherent, white light source with interchangeable fiber bundle (model LC-122, LumaCare) was used in all photoinactivation experiments. The irradiance at the position of the samples was kept at 300 mW/cm$^2$, as measured by a laser power meter (Model 840011, SPER Scientific).

Characterization.

The morphology of the Ag@mSiO$_2$@photosensitizer hybrids was characterized by a Phillips Biotwin 12 transmission electron microscope (FEI). TEM samples were prepared by directly applying 10 μL of the sample ethanol solution onto a carbon-coated copper grid (300 mesh, EMS) and left to dry at room temperature. UV-Vis absorption spectra were measured using a UV-Vis spectrometer (USB4000-ISS, Ocean Optics). The loading efficiency of photosensitizers was determined by measuring the photosensitizers in the supernatant after centrifugation via UV-Vis absorption spectra. The Ag$^+$ concentration was measured by a triple quadruple ICP-MS (ICP-QQQ, Agilent Technologies).

Data Analysis and Statistics.

Each experiment was performed at least in triplicate. The primary data are presented as the means with standard deviations of the mean. Differences are analyzed for statistical significance by the two-sample Student's t-test and the probability values of less than 5% are considered significant.

Ag@mSiO$_2$@photosensitizer Hybrid Resonance Coupling.

The resonance coupling between the photosensitizers and the AgNPs core in the Ag@mSiO$_2$@photosensitizer hybrids was determined. The UV-Vis absorption spectra of all Ag@mSiO$_2$@photosensitizer hybrids were measured. The surface plasmon peak positions in the Ag@mSiO$_2$@photosensitizer hybrids are slightly red-shifted, compared to that of the Ag@mSiO$_2$ nanoparticles at about 403 nm. Different photosensitizers displayed different degrees of resonance coupling with AgNPs depending on the overlap of the surface plasmon and the absorption spectra of the photosensitizers. For example, HPIX, TCPP, Cu-TCPP, PIX, and RuBPy had stronger resonance coupling with the AgNPs core than RB.

Ag@mSiO$_2$@photosensitizer Hybrid Spectral Characteristics.

As discussed above, plasmonic-molecular resonance coupling may form hybrid state(s) with new spectral characteristics. To this end, the fluorescence emission and excitation spectra of the Ag@mSiO$_2$@photosensitizer hybrids and the respective pure photosensitizer were measured. In the case of TCPP, Cu-TCPP, PIX, and HPIX, all common porphyrin derivatives, the Ag@mSiO$_2$@photosensitizer hybrids displayed strong resonance coupling. There were significant changes in the fluorescence emission and excitation spectra of the hybrids, both in intensity and shape. The high-energy Soret band (B-band) and the low-energy quasi-allowed band (Q-band) transitions in the excitation spectra both decreased significantly. The emission bands were broadened and markedly weakened. As the concentrations of photosensitizer increased, the fluorescence intensities decreased greatly due to severe self-quenching. In contrast, Ag@mSiO$_2$@Cu-TCPP displayed only a slight change both in intensity and shape as compared to pure Cu-TCPP. The low fluorescence intensity of pure Cu-TCPP is probably due to the paramagnetic nature of the central copper (II). In the case of RuBPy and RB, the hybrids showed little change in fluorescence emission and excitation spectra, except the quenching increases with the increase of the photosensitizer concentration. Based on the spectra of these six Ag@mSiO$_2$@photosensitizer hybrids, the hybrid state(s) formed by the surface plasmon-molecular resonance coupling is considered to markedly affect the fluorescence of the photosensitizers.

Ag@mSiO$_2$@photosensitizer Hybrid Time-Resolved Photoluminescence.

The time-resolved photoluminescence of the pure photosensitizers and the Ag@mSiO$_2$@photosensitizer hybrids were measured. Results are shown in Table 1, where $\tau_n$ is amplitude-weighted lifetime and an is amplitude. In all cases except Cu-TCPP and RuBPy, the lifetimes of the photosensitizers were greatly reduced by the presence of the hybrid state(s), indicating the energy transfer from the excited states of photosensitizers to the AgNPs core. In the case of Cu-TCPP, the lifetime of the hybrid did not differ much from that of pure Cu-TCPP, because the lifetime of Cu-TCPP is already short due to the paramagnetic copper (II). For the Ag@mSiO$_2$@RuBPy hybrid, the effect on lifetime was insignificant.

Ag@mSiO$_2$@photosensitizer Hybrid Singlet Oxygen Production.

Singlet oxygen production from the Ag@mSiO$_2$@photosensitizer hybrids, the corresponding photosensitizers, and Ag@mSiO$_2$ nanoparticles, respectively, were measured and calculated to determine any enhancement of singlet oxygen from the hybrids. The singlet oxygen enhancement factor (EF) is defined by Equation (3):

$$EF = \frac{(I_h - I_p - I_{Ag})}{I_p}$$

where $I_n$, $I_p$, and $I_{Ag}$ are the singlet oxygen emission intensity of the hybrids, the pure photosensitizers, and AgNPs, respectively. The results showed that hybrids generally demonstrated significant enhancement in singlet oxygen production. The HPIX, TCPP, Cu-TCPP, PIX, and RuBPy hybrids displayed enhanced production of singlet oxygen by up to three orders of magnitude, as compared to the corresponding pure photosensitizers. The only hybrid that did not display enhanced production of singlet oxygen was Ag@mSiO$_2$@RB, most likely because of the weak resonance coupling between RB and AgNPs. The results also show that Ag@mSiO$_2$ nanoparticles themselves can produce some singlet oxygen due to the AgNP core.

Photodynamic Inactivation of Bacteria.

The Ag@mSiO$_2$@photosensitizer hybrids demonstrated very good efficiency in photodynamic inactivation of broad-spectrum bacteria. Ag@mSiO$_2$@HPIX was used as a model system in the PDI study. Ag@mSiO$_2$@HPIX was first tested with *S. epidermidis*, a Gram-positive bacterium. The bacterial culture was mixed with a series of Ag@mSiO$_2$@HPIX hybrids in which the adsorbed HPIX concentration was from 0.125 to 2 µM. The culture and hybrid were immediately irradiated with 40 J/cm$^2$ of white light. There was a dramatic difference in the lethality against *S. epidermidis* among the hybrid, pure HPIX of same concentration, and Ag@mSiO$_2$ nanoparticles. For the hybrid having an adsorbed HPIX concentration of 2 µM, bacterial killing of about 6-log was observed. For comparison, pure HPIX and Ag@mSiO$_2$ nanoparticles displayed less than 1-log bacterial killing under the same conditions. The enhancement in the bacterial killing efficiency can be quantified by Equation (4):

$$\log_{10}(\text{Enhancement Killing}) = \log_{10}(\text{Hybrid Killing}) - \log_{10}(\text{Photosensitizer Killing}) - \log_{10}(\text{AgNPs Killing})$$

For *S. epidermidis*, the Ag@mSiO$_2$@HPIX hybrid displayed an enhancement in bacterial killing efficiency of 5-log when the concentration of the adsorbed HPIX was 2 µM. Parallel experiments conducted without light illumination showed negligible antibacterial effect of the hybrid, as well as pure HPIX and Ag@mSiO$_2$ nanoparticles. While Ag ions in the Ag@mSiO$_2$ nanoparticles can be slowly released into the solution, as shown in our measurements, the antibacterial effect of the released Ag ions appears to be insignificant considering that there is little incubation time after the hybrid is mixed with the bacteria. These results show the synergistic effect of the Ag@mSiO$_2$@photosensitizer hybrids in the PDI against *S. epidermidis*.

The antibacterial effects of the hybrids were also tested against two Gram-negative bacteria, *E. coli* and *A. baumannii*, the latter being a drug-resistant pathogen. The effects of the Ag@mSiO$_2$@HPIX hybrid against *E. coli* and *A. baumannii* were similar to those against *S. epidermidis*. While Ag@mSiO$_2$ nanoparticles exhibited some bacterial killing under a relatively high fluence, the hybrid displayed a higher PDI efficiency than pure HPIX and Ag@mSiO$_2$ nanoparticles. *E. coli* was mixed with the hybrid having an adsorbed HPIX concentration of 1 µM and exposed to a fluence of 400 J/cm$^2$. This resulted in the complete eradiation of the bacteria and an enhancement in bacterial killing of up to 4-log. In the case of *A. baumannii*, the same hybrid may completely eradiate bacteria under a fluence of 200 J/cm$^2$, again with an enhancement in bacterial killing of up to 4-log. These results demonstrate that the Ag@mSiO$_2$@photosensitizer hybrids display synergistic effect in bacterial killing against broad-spectrum bacteria.

Example 2

Synthesis of Ag@mSiO$_2$@Photosensitizer Hybrids.

Ag@mSiO$_2$@HPIX and Ag@mSiO$_2$@Riboflavin hybrids were synthesized according to the method used in Example 1.

Photodynamic Inactivation Assays.

Cultures of *S. epidermidis*, *E. coli*, and *A. baumannii* were inoculated and mixed with a series of concentrations of Ag@mSiO$_2$@HPIX hybrid, HPIX (dissolved in the same PBS buffer solution), or Ag@mSiO$_2$ nanoparticles according to the method in Example 1. PDI assays were conducted on the bacteria and hybrids according to the method used in Example 1. Dark controls were run in parallel. Three independent runs were carried out for each experiment. Different optical filters were used to select the wavelength range of the illumination.

Characterization.

The morphology of the Ag@mSiO$_2$@photosensitizer hybrids, UV-Vis absorption spectra, and loading efficiency of photosensitizers were measured according to the method in Example 1.

Data Analysis and Statistics.

Each experiment was performed at least in triplicate. The primary data are presented as the means with standard deviations. Differences are analyzed for statistical significance by the two-sample t-test and the probability values of <5% are considered significant.

Photodynamic Inactivation of Bacteria.

The Ag@mSiO$_2$@photosensitizer hybrids demonstrated very good efficiency in broad-spectrum photodynamic inactivation of bacteria. Ag@mSiO$_2$@HPIX was used as a model system in the PDI study. Ag@mSiO$_2$@HPIX was first tested against *Staphylococcus epidermidis* (ATCC 35984), a Gram-positive bacterium. The bacterial culture was mixed with a series of Ag@mSiO$_2$@HPIX hybrids in which the adsorbed HPIX concentration was from 0.125 to 2 µM. The mixtures were immediately irradiated with 40 J/cm$^2$ of white light. There was a dramatic difference in the lethality against *S. epidermidis* among the hybrid, pure HPIX of same concentration, and Ag@mSiO$_2$ nanoparticles. For the hybrid, bacterial killing of about 6-log was observed when the adsorbed HPIX concentration in the hybrid was 2 µM. For comparison, pure HPIX and Ag@mSiO$_2$ nanoparticles displayed less than 1-log bacterial killing under the same conditions. For *S. epidermidis*, the Ag@mSiO$_2$@HPIX hybrid displayed an enhancement in bacterial killing efficacy of 5-log when the adsorbed HPIX concentration was 2 µM. Parallel experiments conducted without light illumination show negligible antibacterial effect of the hybrid, pure HPIX, and the Ag@mSiO$_2$ nanoparticles. While Ag ions in the Ag@mSiO$_2$ nanoparticles can be slowly released into the solution, the antibacterial effect of the released Ag ions appears to be insignificant considering that there is little incubation time after the hybrid is mixed with the bacteria. These results demonstrate the synergistic effect of Ag@mSiO$_2$@photosensitizer hybrids in the PDI against *S. epidermidis*.

The antibacterial effect of the hybrids was also tested against two Gram-negative bacteria, *E. coli* and *A. baumannii*, the latter being a drug-resistant pathogen. Both fluence-dependence and concentration-dependence experiments were carried out to illustrate the PDI efficiency of the hybrids. The killing efficacy of the Ag@mSiO$_2$@HPIX hybrid against *E. coli* and *A. baumannii* was similar to that against *S. epidermidis*. While Ag@mSiO$_2$ nanoparticles exhibited some bacterial killing under relatively high fluence, the hybrid displayed a higher PDI efficiency than pure HPIX and Ag@mSiO$_2$ nanoparticles. For *E. coli*, the hybrid with an adsorbed HPIX concentration of 1 µM and under fluence of 400 J/cm$^2$ resulted in the complete eradiation of the bacterium and an enhancement in bacterial killing of up to 4-log. In the case of *A. baumannii*, the same hybrid can completely eradiate the bacterium under fluence of 200 J/cm$^2$, again with an enhancement in bacterial killing of up to 4-log. These results demonstrate the synergistic effect of Ag@mSiO$_2$@photosensitizer hybrids in killing both Gram-positive and Gram-negative bacteria.

The killing efficacy of the Ag@mSiO$_2$@Riboflavin hybrid against *Staphylococcus epidermidis*, *Escherichia coli* and *Acinetobacter baumannii* under visible light and near-infrared irradiations was measured. The pure photosensitizer, Riboflavin, needs visible light excitation to display rather moderate antibacterial effect. In great contrast, the Ag@mSiO$_2$@Riboflavin hybrid demonstrates high efficacy in inactivating bacteria under both visible light and near-infrared light irradiations. The results demonstrate a broadening of the spectral window of excitation.

Example 3

Synthesis of Ag@mSiO$_2$@Photosensitizer Hybrids.
Ag@mSiO$_2$@HPIX hybrid was synthesized similarly as according to the method used in Example 1.
Loading Efficiency and Zeta Potential Measurements.
The loaded HPIX amount in the Ag@mSiO$_2$@HPIX was determined by its fluorescence emission at 630 nm under 400 nm excitation. After comparison with a calibration curve established by a series of HPIX solutions of different concentrations, the loaded amount of HPIX in the Ag@mSiO$_2$@HPIX was calculated as ~0.993 µmol per 100 mg of Ag@mSiO$_2$.

Singlet oxygen generation by the hybrids was experimentally determined by monitoring the phosphorescence emission at ~1280 nm. Under 400 nm excitation, the Ag@mSiO$_2$@HPIX hybrids displayed much higher singlet oxygen generation than the pure HPIX and the Ag@mSiO$_2$ nanoparticles combined, which is consistent with previous observations. The concentration of HPIX in Ag@mSiO$_2$@HPIX hybrids and the pure HPIX solution was kept at ~2.1 µM, whereas Ag@mSiO$_2$ and Ag@mSiO$_2$@HPIX hybrids contained the similar amounts of Ag. Singlet oxygen excitation spectra were also measured for the 1280 nm emission. Ag@mSiO$_2$@HPIX hybrids display a broadened excitation profile into the near-infrared region, implying that the Ag@mSiO$_2$@HPIX hybrids have great potential for applications requiring deep tissue penetration.

The size of the hybrid nanoparticles was determined through transmission electron microscopy (TEM). The diameter of the nanoparticles was found to be ~62 nm, whereas that of the Ag core was ~25 nm and the mesoporous silica shell thickness ~20 nm. The zeta potential of the Ag@mSiO$_2$@HPIX was measured to be −30.3 mV, suggesting good stability in aqueous solutions.

Cytotoxicity of AG©mSiO$_2$@HPIX Hybrids on Primary Dermal Fibroblast Cells Under Light Illumination.

Cytotoxicity of the Ag@mSiO$_2$@HPIX hybrids on the primary dermal fibroblast cells was evaluated. The primary dermal fibroblast; normal, human, adult cells (HDFa) (ATCC PCS-201-012) were treated with different concentrations of the Ag@mSiO$_2$@HPIX hybrids and incubated for 24 h, before being illuminated by an LED for 45 min (400 nm, 54 mW/cm2). Then, the viabilities of the ATCC PCS-201-012 cells were determined by MTT assay. Under light illumination, the photo-cytotoxicity of the Ag@mSiO$_2$@HPIX hybrids at concentrations up to 0.5 µM is negligible. At the highest tested concentration of 4.2 µM, the cell viability is still ~80%.

Photodynamic Inactivation of *T. rubrum*.

The in vitro PDI of *T. rubrum* (ATCC 28188) was investigated using different concentrations of Ag@mSiO$_2$@HPIX hybrids, pure HPIX and Ag@mSiO$_2$. Control experiments were carried out without the LED illumination. None of the Ag@mSiO$_2$@HPIX hybrids, pure HPIX or Ag@mSiO$_2$ at the tested concentrations shows antifungal effect without LED illumination. Separately, *T. rubrum* samples were treated with an LED light source (400 nm, 54 mW/cm2), after incubating for 30 min. with different concentrations of the Ag@mSiO$_2$@HPIX hybrids, free HPIX, and Ag@mSiO$_2$, respectively. An LED was used as the light source because the LED does not cause a thermal effect to the samples. Plate count method was employed to determine the viable fungal count, after the growth of the *T. rubrum* became visible. The data collected demonstrates that the pure HPIX and Ag@mSiO$_2$ have negligible PDI efficacy on *T. rubrum* under these experimental conditions. In contrast, significant killing of *T. rubrum* treated with Ag@mSiO$_2$@HPIX hybrids under the same conditions was observed, suggesting the synergistic effect of the Ag core and HPIX in the Ag@mSiO$_2$@HPIX hybrids. In these experiments, the pure HPIX and Ag@mSiO$_2$@HPIX hybrids have the same concentration of HPIX while the amounts of Ag in Ag@mSiO$_2$@HPIX hybrids and Ag@mSiO$_2$ was also kept constant.

The enhancement of antifungal PDI efficacy of Ag@mSiO$_2$@HPIX hybrids is defined as $$\log_{10}(\text{enhancement}) = \log_{10}(\text{Ag@mSiO}_2\text{@HPIX\_killing}) - \log_{10}(\text{Ag@mSiO}_2\text{\_killing}) - \log_{10}(\text{HPIX\_killing})$$

Overall PDI efficacy of up to 3-orders of magnitude is observed for the Ag@mSiO$_2$@HPIX hybrids against *T. rubrum*, which is hundreds of times more effective than pure HPIX and the Ag@mSiO$_2$ nanoparticles acting separately. Even at low concentrations of the Ag@mSiO$_2$@HPIX hybrids (0.4 and 0.5 µM), there are significant enhancements in PDI efficacy of ~2.5 orders of magnitude. These results are consistent with the data in the singlet oxygen generation experiments and demonstrate the advantage of the hybrid photosensitizers.

While all of the invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicants' general inventive concept.

What is claimed is:

1. A method of killing fungi comprising:
   contacting fungi with a nanostructure comprising a silver nanoparticle core, a mesoporous silica shell, and a photosensitizer to form a blend; and
   exposing said blend to light.

2. The method claimed in claim 1, wherein said fungi is *Tricophyton rubrum*.

3. The method claimed in claim 1, wherein the light is produced by a light emitting diode.

4. The method claimed in claim 1, wherein said light has a broad spectrum, the broad spectrum including visible and near infrared wavelengths.

5. The method of claim 1, wherein said blend comprises a Ag@mSiO2@HPIX hybrid.

* * * * *